(12) United States Patent
Ramey et al.

(10) Patent No.: US 8,092,428 B2
(45) Date of Patent: Jan. 10, 2012

(54) METHODS AND SYSTEMS FOR ADJUSTING AN INSULIN DELIVERY PROFILE OF AN INSULIN PUMP

(75) Inventors: Blaine Edward Ramey, Indianapolis, IN (US); Rick Collins, Cicero, IN (US); James Pauley, Fishers, IN (US); Robert David Timmerman, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 9 days.

(21) Appl. No.: 12/645,587

(22) Filed: Dec. 23, 2009

(65) Prior Publication Data

US 2011/0152769 A1 Jun. 23, 2011

(51) Int. Cl.
*A61M 1/00* (2006.01)
(52) U.S. Cl. ........................................................ 604/151
(58) Field of Classification Search .................. 604/65, 604/151, 890.1, 818.1, 892.1; 600/365
See application file for complete search history.

(56) References Cited

U.S. PATENT DOCUMENTS

| | | | |
|---|---|---|---|
| 5,569,186 A | 10/1996 | Lord et al. | |
| 6,198,696 B1 | 3/2001 | Korpi et al. | |
| 7,224,643 B2 | 5/2007 | Morris | |
| 7,717,903 B2* | 5/2010 | Estes et al. | 604/890.1 |
| 2002/0147135 A1* | 10/2002 | Schnell | 514/3 |
| 2002/0198513 A1* | 12/2002 | Lebel et al. | 604/891.1 |
| 2003/0212379 A1 | 11/2003 | Bylund | |
| 2005/0020996 A1 | 1/2005 | Hartlaub et al. | |
| 2005/0021367 A1 | 1/2005 | Saeger et al. | |
| 2007/0093935 A1 | 4/2007 | Fu | |
| 2007/0142822 A1 | 6/2007 | Remde | |
| 2008/0089313 A1 | 4/2008 | Cayo et al. | |
| 2008/0194934 A1* | 8/2008 | Ray et al. | 600/347 |
| 2008/0319295 A1 | 12/2008 | Bernstein et al. | |
| 2009/0069745 A1* | 3/2009 | Estes et al. | 604/67 |
| 2009/0163793 A1 | 6/2009 | Koehler et al. | |

(Continued)

FOREIGN PATENT DOCUMENTS

DE 202004006448 U1 8/2008

(Continued)

OTHER PUBLICATIONS

Trickle-Charge Timekeeping Chip DS1302, www.maxim-ic.com, pp. 1-13.

(Continued)

*Primary Examiner* — Nicholas Lucchesi
*Assistant Examiner* — Aarti B Berdichevsky
(74) *Attorney, Agent, or Firm* — Dinsmore & Shohl LLP

(57) ABSTRACT

Systems and methods are disclosed for adjusting the delivery times of an insulin delivery profile of an insulin pump, wherein the insulin pump is operable to automatically deliver insulin to a person having diabetes based on an operating time of the internal clock and a delivery time of an insulin delivery profile. The method may comprise receiving a local time zone time from an external local clock, determining whether the operating time of the internal clock differs from the local time zone time by at least a first predetermined amount of time, requesting the person provide a time adjustment value when the operating time of the internal clock differs from the local time zone time by at least the first predetermined amount of time, receiving the time adjustment value from the person, and adjusting the delivery times of the insulin delivery profile based on the time adjustment value when received.

37 Claims, 3 Drawing Sheets

U.S. PATENT DOCUMENTS

| | | |
|---|---|---|
| 2010/0069890 A1 | 3/2010 | Graskov et al. |
| 2011/0009725 A1* | 1/2011 | Hill et al. .................. 600/365 |
| 2011/0053121 A1* | 3/2011 | Heaton .................. 434/127 |

FOREIGN PATENT DOCUMENTS

| | | |
|---|---|---|
| WO | 0029047 A1 | 5/2000 |
| WO | 2009/005952 A2 | 1/2009 |

OTHER PUBLICATIONS

Daniel J. Crowe, M.D., et al., Time Synching or Time Sinking, Diabetes Technology & Therapeutics, vol. 7, No. 5, 2005, pp. 663-664.

Chandran, M. & Edelman, S.V. Have insulin, will fly: Diabetes management during air travel and time zone adjustment strategies. Clinical Diabetes 21, 82-85 (2003).

Kruskal, J.B. An overview of sequence comparison: Time warps, string edits, and macromolecules. SIAM Review 25, 201-207 (1983).

Sane, T., Koivisto, V.A., Nikkanen, P. & Pelkonen, R. Adjustment of insulin doses of diabetic patients during long distance flights. BMJ301, 421-422 (1990).

International Search Report and Written Opinion pertaining to International patent application No. PCT/US2010/060924, dated Jun. 22, 2011.

* cited by examiner

METHODS AND SYSTEMS FOR ADJUSTING AN INSULIN DELIVERY PROFILE OF AN INSULIN PUMP

TECHNICAL FIELD

Embodiments of the present invention generally relate to insulin pumps and, specifically, to updating the insulin delivery profile of an insulin pump.

BACKGROUND

As background, people suffer from either Type I or Type II diabetes in which the sugar level in the blood is not properly regulated by the body. As a consequence, many people with diabetes often use insulin pumps in order to automatically deliver a dose of insulin throughout the day. These insulin pumps often have an internal clock which is used to determine when to deliver the insulin to the person according to the operating times of an insulin delivery profile, which may be established by a health care provider. People who use insulin pumps may travel across one or more time zones and, thus, may need to adjust the insulin delivery profile of the insulin pump based on their own internal clock as well as the local time zone.

SUMMARY

It is against the above background that embodiments according to the present invention are provided which recognize when the user's local time has changed and permit the user to adjust the insulin delivery profile of the insulin pump, based on the user's preference and the difference in time between the internal clock of the insulin pump and the local time zone.

In one embodiment, an insulin pump for automatically delivering insulin to a person having diabetes and configured to receive at least a local time zone time from an external local clock comprises: an internal clock providing an operating time; a delivery module for delivering the insulin to the person; memory storing an insulin delivery profile comprising one or more delivery times; a wireless communication module configured to wirelessly receive the local time zone time from the external local clock; and a processor in electrical communication with the internal clock, the memory for reading the insulin delivery profile, the delivery module, and the wireless communication module, wherein the processor: automatically causes the delivery module to deliver the insulin to the person when a delivery time of the insulin delivery profile that is read from memory by the processor matches the operating time of the internal clock, receives the local time zone time from the wireless communication module, makes a request for the person to provide a time adjustment value when the operating time of the internal clock differs from the local time zone time by at least a first predetermined amount of time, receives the time adjustment value from input provided by the person, and adjusts the one or more delivery times of the insulin delivery profile based on the time adjustment value when received.

In another embodiment, a system for automatically delivering insulin to a person having diabetes and configured to receive at least a local time zone time from an external local clock comprises: an insulin pump having: an internal clock providing an operating time, a delivery module for delivering the insulin to the person according to an insulin delivery profile comprising one or more delivery times, memory storing the insulin delivery profile, and a first processor in electrical communication with the internal clock, the memory for reading the insulin delivery profile, and the delivery module; and a blood glucose (bG) meter in communication with the insulin pump via a communication link, the bG meter having an input device, a display, a wireless communication module, and a second processor in electrical communication with the input device, the display, the wireless communication module, wherein: the second processor: receives the operating time of the internal clock of the insulin pump via the communication link, receives the local time zone time from the external local clock via the wireless communication module or from the person via the input device, determines whether times of the local time zone time and the operating time differ by at least a first predetermined amount of time, displays a request on the display for a time adjustment value from the person representing an amount of time to adjust the one or more delivery times of the insulin delivery profile when the operating time of the internal clock differs from the local time zone time by at least the first predetermined amount of time, receives the time adjustment value via the input device, sends the time adjustment value when received to the insulin pump via the communication link, and the first processor adjusts the one or more delivery times of the insulin delivery profile based on the time adjustment value sent from the bG meter.

In still another embodiment, a method for adjusting an insulin delivery profile of an insulin pump, wherein the insulin pump is configured to automatically deliver insulin to a person having diabetes based on an operating time of the internal clock and an insulin delivery profile comprising one or more delivery times, comprises: receiving a local time zone time from an external local clock; determining whether the operating time of the internal clock differs from the local time zone time by at least a first predetermined amount of time; requesting the person provide a time adjustment value when the operating time of the internal clock differs from the local time zone time by at least the first predetermined amount of time; receiving the time adjustment value from the person; and adjusting the one or more delivery times of the insulin delivery profile based on the time adjustment value when received.

These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods and systems for updating the insulin delivery profile of an insulin pump. The insulin pump may comprise an internal clock which is configured to maintain the operating time for the insulin pump, which may include the date and year. People who use insulin pumps may travel across one or more time zones and, thus, may need to adjust the internal clock of the insulin pump, based on their own internal clock as well as the local time zone.

For the purposes of defining and describing the present disclosure, the term "UTC" refers to Coordinated Universal Time, which is a time standard based on International Atomic Time (TAI). UTC is independent of time zones such that it is exactly the same throughout the world. Most of the time zones in the world are related to UTC by a multiple of one hour. For example, the Eastern Time Zone in the United States is five hours earlier than UTC during standard time (UTC-5) and four hours during daylight savings time (UTC-4).

For the purposes of defining and describing the present disclosure, the term "local time zone" refers to the time zone in which the person using the insulin pump is located. A "local time zone time" is the current time in the local time zone.

For the purposes of defining and describing the present disclosure, the term "internal clock" refers to the internal clock of the insulin pump. The internal clock may operate independently of the local time zone; that is, it may have its own power supply, frequency source, etc. An operating time of the internal clock refers to the current time according to the internal clock.

For the purposes of defining and describing the present disclosure, wireless communication refers to the transmission of data or information without the use of physical conductors or "wires." One type of wireless communication may be radio frequency, or "RF," in which the data is transmitted via electromagnetic waves. For example, "Bluetooth®" is one type of wireless RF communication system which uses a frequency of approximately 2.4 Gigahertz (GHz). Another type of wireless communication scheme may use infrared light, such the systems supported by the Infrared Data Association® (IrDA®). Other types of wireless communication are also contemplated, including present technologies and yet-to-be developed technologies.

Figure 1:
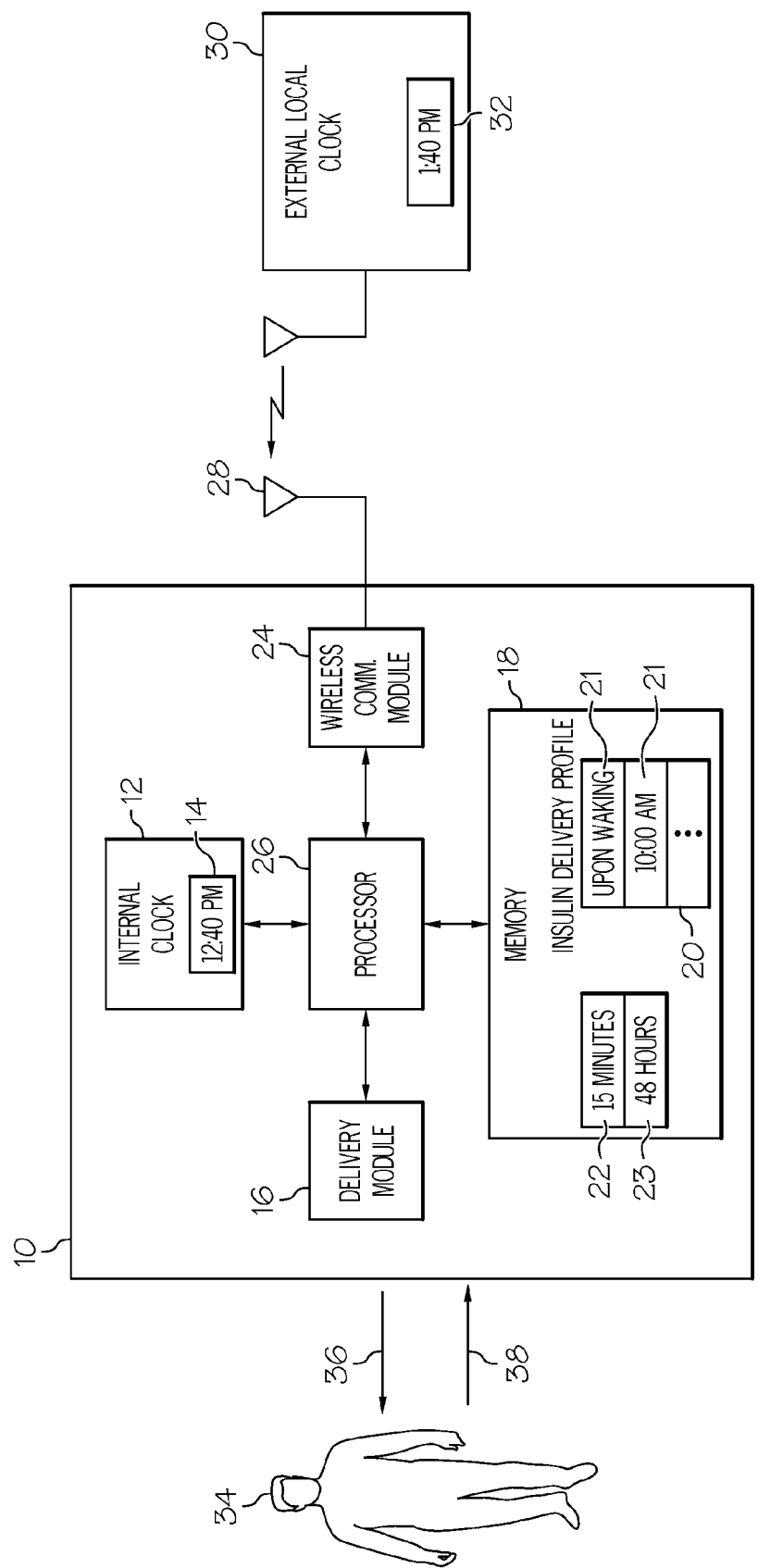
FIG. 1 depicts an insulin pump for automatically delivering insulin to a person according to one or more embodiments shown and described herein.

FIG. 1 depicts an insulin pump 10 according to one embodiment of the present disclosure. The insulin pump 10 may comprise an internal clock 12, a delivery module 16, memory 18, a wireless communication module 24, and a processor 26. The internal clock 12 may provide an operating time 14 for the insulin pump 10. The internal clock 12 may be in electrical communication with the processor 26 such that the processor 26 is configured to read an operating time 14 from the internal clock 12. The internal clock 12 may comprise an integrated circuit (not shown), a crystal (not shown), or other suitable components as is known in the art. The internal clock 12 may further comprise a number of data registers (not shown) which are configured to maintain data regarding the operating time, date, and year. The processor 26 may operate to periodically read the data registers such as, for example, approximately every minute. As one alternative, the internal clock 12 may be configured to generate an interrupt to the processor 26 every one second or other suitable time period. The internal clock 12 may operate independently from the local time zone time 32; that is, it may operate without any regard to the local time zone time 32. As such, the internal clock 12 may deviate from the external local clock 30 due to, for example, component variations and/or temperature dependencies.

The internal clock 12 may be set to the local time zone in which the person normally lives and works. For example, if the person lives in New York City, the person may set the internal clock 12 to the Eastern Time Zone of the United States. As an alternative, the internal clock 12 may be set to UTC time, which is the same throughout the world. In this alternative, the insulin pump 10 may have one or more data registers (e.g., in the internal clock 12, memory 18, or processor 26) which indicate the difference in the local time zone and UTC. In the New York City example from above, the internal clock 12 may be set to UTC, and a register in the memory 18 may indicate that the local time zone time is UTC-5, that is five hours behind UTC. In this example, "adjusting the internal clock 12" may comprise adjusting the register in the memory 18 which indicates the difference between the internal clock (set to UTC) and the desired operating time. Other similar techniques may be used to set the operating time 14 of the internal clock 12 as well.

The delivery module 16 may be in electrical communication with the processor 26 and may be configured to deliver insulin to the person 34. The delivery module 16 may include a cannula (not shown) and associated tubing (not shown) for allowing subcutaneous injection of the insulin. Accordingly, the delivery module 16 may be physically coupled to the person 34 in order to facilitate the delivery of the insulin. Other types of delivery modules, both in known the present art and yet to be discovered, are contemplated as well.

The memory 18 may be in electrical communication with the processor 26 and may comprise an insulin delivery profile 20 which may comprise one or more delivery times 21 so as to provide a schedule for delivering insulin to the person 34 based, at least in part, on the operating time 14 of the internal clock 12. The one or more delivery times 21 may include a basal rate delivery time. For example, the insulin delivery profile 20 may deliver a basal rate at 11:00 pm, before the person 34 goes to sleep. The insulin delivery profile 20 may also be based on when the person eats a meal. As another example, the insulin delivery profile 20 may delivery a bolus rate when the person 34 indicates that he is eating lunch. As such, the delivery times 21 may be based on time, an event, or combinations thereof. Other types of insulin delivery profiles 20 may be used and may be based on the operating time 14 of the internal clock 12 as well as other factors.

The memory 18 may comprise static random access memory (RAM), flash memory, electrically-erasable programmable read only memory (EEPROM), or other suitable memory. The memory 18 may store the insulin delivery profile 20 as well as other information. The memory 18 may be a non-volatile memory such that it retains its contents even after power is removed from the insulin pump (e.g., when changing batteries). In one embodiment, the memory 18 may be a separate integrated circuit in the insulin pump 10. In another embodiment, the memory 18 may be integrated into the processor 26 along with other peripheral components, such as timers, interrupt controllers, and so forth. In still another embodiment, the memory 18 may be integrated into an application specific integrated circuit (ASIC) along with other suitable components, such as the processor 26, the internal clock 12, and/or the wireless communication module 24. Other embodiments of the memory 18 are also contemplated.

The wireless communication module 24 may be in electrical communication with the processor 26 and may be configured to wirelessly receive the local time zone time 32 from the external local clock 30. The wireless communication module 24 may be coupled to an antenna 28 in order to facilitate the receiving and/or sending of data. The antenna 28 may either be internal or external to the insulin pump 10. The wireless communication module 24 may comprise a communications processor and/or other suitable components, as is known in the art. The wireless communication module 24 may be configured to wirelessly receive the local time zone time 32 from the external local clock 30.

The processor 26 may be a microprocessor, microcontroller, or other suitable device. In one embodiment, the processor 26 may be a low-cost, high-performance HCS08 Family of n-bit microcontroller units (where "n" is greater than or equal to 8) that is provided with a variety of modules, memory sizes, memory types, and package types. In one particular embodiment, the processor 26 is a Freescale Semiconductor MC9S08JM60 chip providing an enhanced HCS08 central processing unit core programmable via HC08 instructions, and providing an internal addressable bus with on-chip in-circuit programmable flash memory. In other embodiments, other microcontrollers and/or microprocessors may similarly be used, including those made or provided by different manufacturers, such as for example, microcontrollers from Microchip Technology, Inc. The processor 26 may execute programming instructions (residing in either on-chip or off-chip memory) which embody the tasks the processor 26 is to perform.

The external local clock 30 may be derived from a global positioning system, a wireless computer network, a cellular network, a blood glucose meter, or a smart phone. As one example, the external local clock 30 may be derived from a local wireless computer network, such as IEEE 802.11, from which the insulin pump 10 may receive the local time zone time (which may include the date and year.) In this example, one of the devices of the network may comprise an external local clock 30 which represents the time in the local time zone. This external local clock 30 may be configured to transmit the local time zone time over the IEEE 802.11 network and to the insulin pump 10. The external local clock 30 may be derived from other systems as well, as is known in the art or yet to be discovered. In yet another embodiment, the external local clock 30 may be derived from a telephony network, such as the third- or fourth-generation (3G or 4G) cellular network, from which the insulin pump may receive the actual time and/or actual time zone information. Thus, the insulin pump 10 may receive the local time zone time 32 either directly or indirectly from the external local clock 30.

In yet another embodiment, the external local clock 30 may be derived from a global positioning system. In this embodiment, the insulin pump 10 may be configured to receive satellite signals from the global positioning system (GPS) currently in operation in the United States and other parts of the world. The insulin pump 10 may then be configured to calculate its global position, based on the GPS signals, which may further contain information regarding the UTC time. The insulin pump 10 may be configured to determine in which time zone it is located (based on the position calculation) and may be configured to derive the local time zone time, based on the position calculation and the UTC time received from the GPS signals.

The processor 26 may be in electrical communication with the internal clock 12, the delivery module 16, the memory 18 for reading the insulin delivery profile 20, and the wireless communication module 24. The processor may be configured to automatically cause the delivery module 16 to deliver insulin to the person 34 when a delivery time of the insulin delivery profile 20 that is read from memory 18 by the processor 26 matches the operating time 14 of the internal clock 12. The processor 26 can automatically cause insulin to be delivered to the person in this fashion since it may execute programming instructions directing it to do so. The processor 26 may also be configured to receive the local time zone time 32 from the wireless communication module 24. The processor 26 may be configured to make a request 36 to the person 34 to provide a time adjustment value 38 when the operating time 14 of the internal clock 12 differs from the local time zone time 32 by at least a first predetermined amount of time 22.

The processor 26 may further be configured to receive the time adjustment value 38 from the wireless communication module 24 and to adjust the delivery times 21 of the insulin delivery profile accordingly. This may be accomplished in a number of ways. In one embodiment, they may be adjusted by simply adjusting each delivery time by the appropriate amount of time. For example, if the person wanted to set forward the insulin delivery profile by three hours, the person may set forward each delivery time by three hours. This may be done all at once or on an individual delivery time basis. Note that delivery times which are solely based on an event (and not time) may not be affected by this adjustment. As an alternative embodiment, all of the delivery times 21 may be adjusted at the same time by adjusting the operating time 14 of the internal clock 12, based on the time adjustment value 38 when received. In yet another embodiment, the insulin pump may have an "adjustment register" which provides a time adjustment for the internal clock 12 when used to compare its current time to the delivery times 21 of the insulin delivery profile 20 (when determining whether to deliver insulin to the person). Other techniques may be used to adjust the delivery times 21 of the insulin delivery profile 20 as well. If adjusting the delivery times 21 does not require that the internal clock 12 be adjusted, the person may also be able to adjust the internal clock 12 separately from adjusting the delivery times 21. Both adjustments may be done at the same time or at separate times.

The processor 26 may further be configured to periodically request a local time zone time update from the wireless communication module 24. For example, the processor 26 may request a local time zone update every five minutes (e.g., based on the operating time 14 of the internal clock 12). As an alternative, the processor 26 may request a local time zone update whenever it causes the delivery module 16 to deliver insulin to the person 34. In still another embodiment, the processor 26 may request a time zone update whenever the wireless communication module 24 establishes connection with the external local clock 30 (since the wireless connection between the wireless communication module 24 and the external local clock 30 may be broken throughout the course of a day.) Other techniques of deciding when to request a local time zone time update may be used as well.

Upon making a request 36 that the person 34 to provide a time adjustment value 38, the processor 26 may be further configured to limit the time adjustment value to the difference between the operating time 14 of the internal clock 12 and the local time zone time 32 of the external local clock 30. For example, if the person in the United States travels from the Eastern Time Zone to the Central Time Zone, the processor 26 may limit the time adjustment value to one hour, since that is the difference between these two time zones.

In another example, the person may travel from the Eastern Time Zone of the United States to the Middle European Time Zone, a difference of six hours. The person may gradually adjust the delivery times 21 of the insulin pump 10, for example, by adjusting the delivery times 21 one hour per day for six consecutive days. Alternatively, the person may adjust the delivery times 21 by one hour one day, and by three hours on another day. In short, any number of adjustments is contemplated, since they may be based on the person's own internal clock and how he or she feels on each day. The processor 26, however, may limit the time adjustment value to the difference in the operating time 14 and the local time zone time 32.

As previously discussed herein, the processor 26 may make a request that the person 34 provide a time adjustment value 38 when the operating time 14 of the internal clock 12 differs from the local time zone time 32 by at least a first predetermined amount of time 22. The first predetermined amount of time 22 may be a suitable amount of time, such as for example 15 minutes. In this example, the processor 26 will not request a time adjustment value 38 unless the difference in time is at least 15 minutes. Thus, if the time difference is only 12 minutes, the processor 26 will not request a time adjustment value 38; similarly, the if the time difference is 15 minutes or more, the processor 26 will request a time adjustment value 38. Other values for the first predetermined amount of time 22 may be used as well. As indicated in FIG. 1, the first predetermined amount of time 22 may be stored in the memory 18. Alternatively, it may be stored in the processor 26.

It is to be noted that, in addition to receiving the local time zone time 32 from an external local clock 30, the insulin pump 10 may also periodically receive adjustments from another external source (not shown) in order to make minor corrections to its internal clock 12. For example, the insulin pump 10 may be configured to wirelessly receive electronic transmissions from radio station WWVB, located in Colorado, which may permit the insulin pump 10 to make minor corrections to its internal clock 12, although the electronic transmissions from WWVB do not provide any time zone information (i.e., WWVB may only provide the UTC time). These minor adjustments may compensate for component variations of the internal clock 12 due to, for example, temperature variations, manufacturing tolerance, etc.

The first predetermined amount of time may be 15 minutes, 30 minutes, 90 minutes, two hours, or any suitable amount of time. In one embodiment, the first predetermined amount of time may be 15 minutes. This may prevent the person from being asked to provide a time adjustment value unless the person travels to a different time zone or the time in the person's time zone changes due to the activation or de-activation of daylight savings time. The first predetermined amount of time may be preset by the manufacturer of the insulin pump or bG meter. Alternatively, the first predetermined amount of time may be settable by the person. That is, the insulin pump or bG meter may permit the person to enter any suitable amount of time. For example, the person may set the first predetermined amount of time to 15 minutes while he is not traveling, and may set it to some other amount of time when traveling. The first predetermined amount of time may be entered in the same fashion as the time adjustment value. In another embodiment, the insulin pump and/or bG meter may have two operating modes: a travel mode of operation and a home mode of operation. In the travel mode of operation, the first predetermined amount of time may automatically be set to a travel value, such as two hours for example. In the home mode of operation, it may automatically be set to a home time, such as 15 minutes for example.

The processor 26 may also delay in making the request 36 for the person 34 to provide a time adjustment value 38 until the operating time of the internal clock differs from the local time zone time by at least the first predetermined amount of time and the difference has persisted for at least a second predetermined amount of time 23. This second predetermined amount of time 23 may be, as an example, 24 hours. In this case, the person traveling to a different time zone will not be bothered with a request to provide a time adjustment value 38 until 24 hours after traveling to the new time zone. This may prevent "nuisance requests" by the insulin pump 10 if the person 34 travels to a neighboring time zone and returns home in the same day. The second predetermined amount of time 23 may be set to other values as well, such as 48 hours or 72 hours. In one embodiment, the second predetermined amount of time may be settable by the person. As indicated in FIG. 1, the second predetermined amount of time 23 may be stored in the memory 18. As an alternative, it may be stored in the processor 26.

The processor 26 may be configured to record a time-stamp of both the local time zone time 32 and the operating time 14 when the insulin is delivered to the person 34. This may permit (when the operating time and the local time zone time are different) the insulin pump to remove any ambiguity as to when the insulin was delivered to the person.

Figure 2:
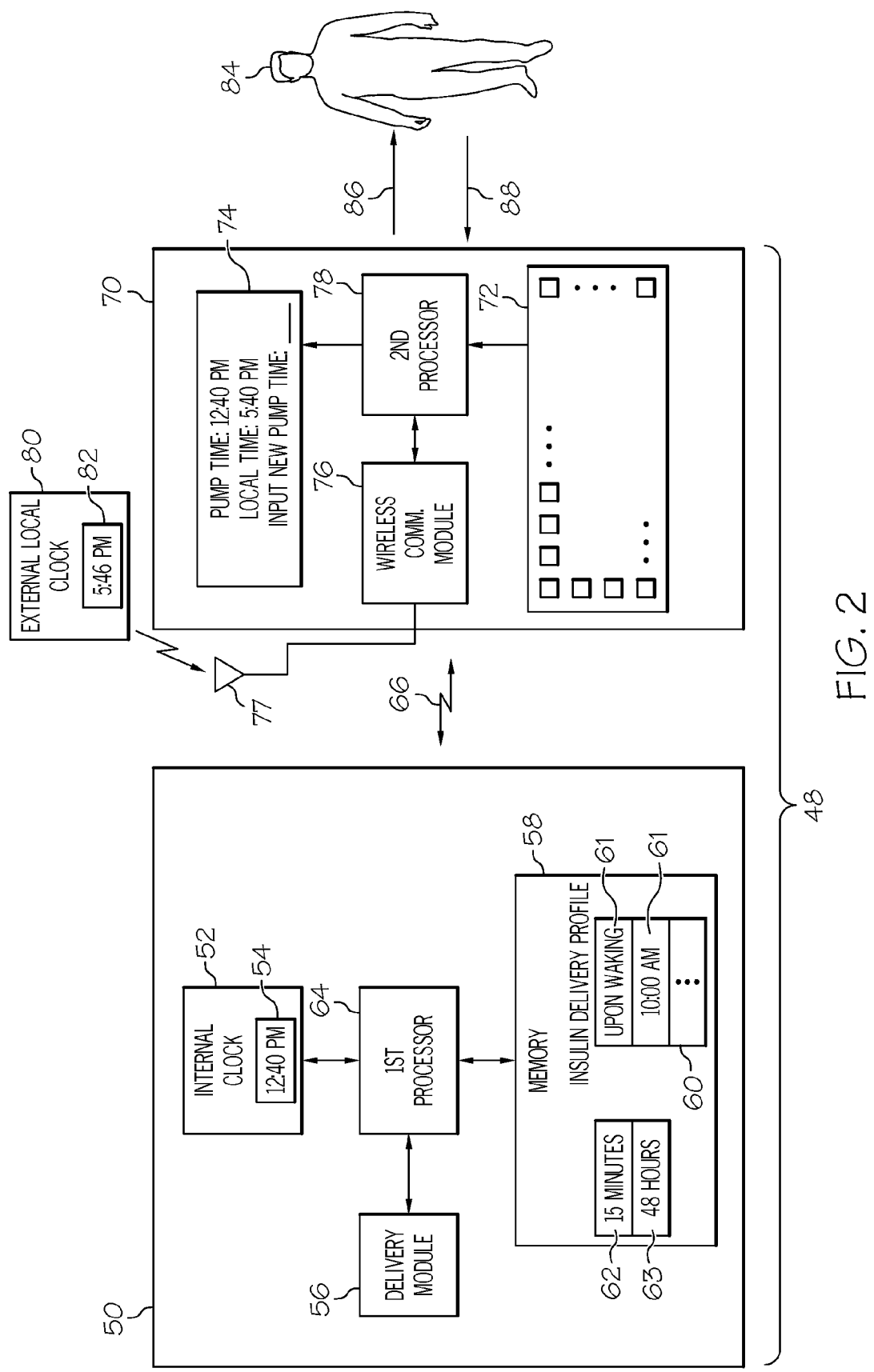
FIG. 2 depicts system for automatically delivering insulin to a person according to one or more embodiments shown and described herein.

FIG. 2 depicts a system 48 for automatically delivering insulin to a person 84 having diabetes and configured to receive at least a local time zone time 82 from an external local clock 80. The system 48 may comprise an insulin pump 50 and a blood glucose (bG) meter 70. The insulin pump 50 may comprise an internal clock 52 providing an operating time 54, a delivery module 56 for delivering the insulin to the person 84, memory 58 for storing an insulin delivery profile 60, and a first processor 64 in electrical communication with the internal clock 52, the memory 58 for reading the insulin delivery profile 60 comprising one or more delivery times 61, and the delivery module 56. The internal clock 52, operating time 54, delivery module 56, memory 58, and insulin delivery profile 60 all may function in a similar fashion to their counterparts shown in FIG. 1 and previously described herein. Similarly, the first processor 64 may also function in a similar fashion to its counterpart, the processor 26 as shown in FIG. 1 and previously described herein.

The bG meter 70 may be in electrical communication with the insulin pump 50 via the wireless communication link 66. The bG meter 70 may comprise an input device 72, a display 74, a wireless communication module 76, and a second processor 78. The second processor 78 may be in electrical communication with the input device 72, which may comprise a keyboard or other suitable component. The input device 72 may comprise a "hard keyboard," which has physical, dedicated buttons the person 84 may press. Alternatively, input device 72 may comprise a touch screen (not shown), which permits the person 84 to enter information by pressing certain locations on the display 74. Other types of input devices may be used as well, as is known in the art. The second processor 78 may be in electrical communication with the input device 72 such that the second processor 78 is configured to read data entered by the person 84. For example, the second processor 78 is configured to receive the time adjustment value 88 from the input device 72, which was input by the person 84.

The display 74 may be in electrical communication with the second processor 78 such that the display 74 is configured to display information and/or messages from the second processor 78. For example, the display 74 may display a message requesting the person 84 enter a time adjustment value 88 representing an amount of time to adjust the internal clock 52 when the operating time 54 of the internal clock 52 differs from the local time zone time 82 by at least the first predetermined amount of time 62. The display 74 may also display other types of messages and or information to the person 84. The display 74 may be a liquid crystal display (LCD) or other suitable display.

The wireless communication module 76 may be in electrical communication with the second processor 78 such that the second processor 78 may read the local time zone time 82 from the wireless communication module 76. The wireless communication module may wirelessly receive the local time zone time 82 from the external local clock 80. The wireless communication module 76 may function similarly to the wireless communication module 24 of FIG. 1 as previously described herein. That is, the wireless communication module 76 may be configured to wirelessly receive the local time zone time 82 derived from a global positioning system, a wireless computer network, a cellular network, another blood glucose meter, or a smart phone.

The second processor 78 is further configured to wirelessly communicate to the insulin pump 50 via the wireless communication link 66. This wireless communication link 66 may be based on, inter alia, radio frequency (RF) or infrared light technology. For example, the wireless communication link 66 may be Bluetooth® or may be a protocol defined by the Infrared Data Association® (IrDA®). Other technologies may be used as well. The wireless communication link 66 may be configured to send the time adjustment value 88, when received by the bG meter 70, to the insulin pump 50. Then, the first processor 64 may be configured to adjust the operating time 54 of the internal clock 52 based on the time adjustment value 88 sent from the bG meter 70.

The second processor 78 may be a microprocessor, microcontroller, or other suitable device. In one embodiment, the second processor 78 may be a low-cost, high-performance HCS08 Family of n-bit microcontroller units (where n is greater than or equal to 8) that is provided with a variety of modules, memory sizes, memory types, and package types. In one particular embodiment, the second processor 78 is a Freescale Semiconductor MC9S08JM60 chip providing an enhanced HCS08 central processing unit core programmable via HC08 instructions, and providing an internal addressable bus with on-chip in-circuit programmable flash memory. In other embodiments, other microcontrollers and/or microprocessors may similarly be used, including those made or provided by different manufacturers, such as for example, microcontrollers from Microchip Technology, Inc. The second processor 78 may execute programming instructions (residing in either on-chip or off-chip memory) which embody the tasks the second processor 78 is to perform.

The second processor 78 may further be configured to periodically request a local time zone time update from the wireless communication module 76. For example, the second processor 78 may request a local time zone update every five minutes (e.g., based on a timer associated therewith). As an alternative, the second processor 78 may request a time zone update whenever the wireless communication module 76 establishes connection with the external local clock 80 (since the wireless connection between the wireless communication module 76 and the external local clock 80 may be broken throughout the course of a day.) Other techniques of deciding when to request a local time zone time update may be used as well.

The first processor 64 or second processor 78 may be configured to limit the time adjustment value 88 to the difference between the operating time 54 of the internal clock 52 and the local time zone time 82 of the external local clock 80. For example, if the difference between the two is three hours and twenty minutes, the first or second processor may limit the time adjustment value to three hours and twenty minutes.

The first predetermined amount of time 62 may be 15 minutes or some other suitable value. The second processor 78 may also delay in making the request 86 for the person 84 to provide a time adjustment value 88 until after the difference (between the internal clock 52 and the external local clock 80) has persisted for at least a second predetermined amount of time 63. This second predetermined amount of time 63 may be, as an example, 24 hours. In this case, the person traveling to a different time zone will not be bothered with a request to provide a time adjustment value 88 until 24 hours after traveling to the new time zone. This may prevent "nuisance requests" by the insulin pump 50 if the person 84 travels to a neighboring time zone and returns home in the same day. The second predetermined amount of time 63 may be set to other values as well, such as 48 hours or 72 hours. As indicated in FIG. 2, the first predetermined amount of time 62 may be stored in the memory 58. As one alternative, it may be stored in the first processor 64 as well. The second predetermined amount of time 63 may be stored in the second processor 78 or any other suitable component coupled to the second processor 78.

The first processor 64 or the second processor 78 may be configured to record a time-stamp of both the local time zone time 82 and the operating time 54 when the insulin is delivered to the person 84. This may permit (when the operating time and the local time zone time are different) the insulin pump to remove any ambiguity as to when the insulin was delivered to the person.

Figure 3:
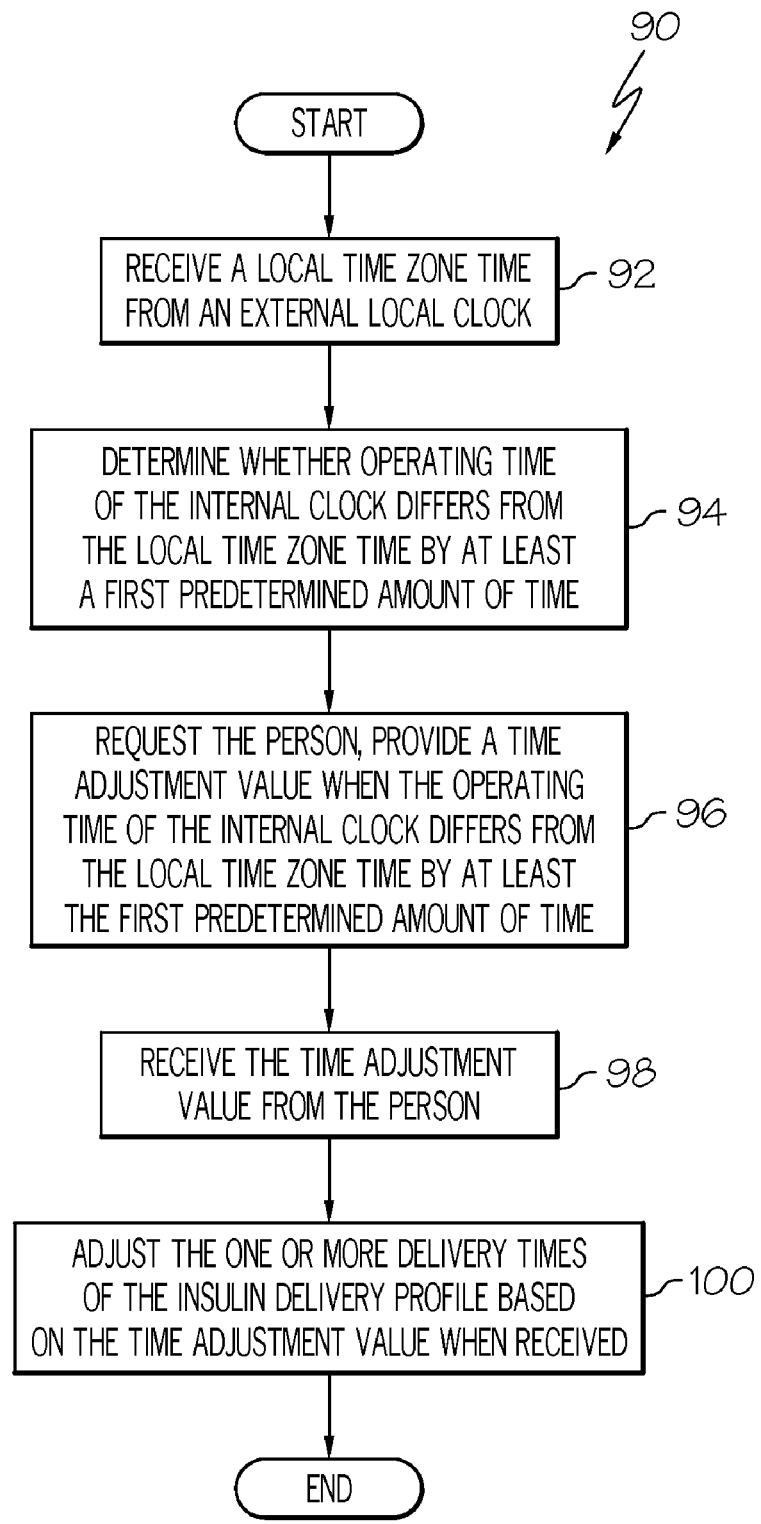
FIG. 3 depicts a method for adjusting an insulin delivery profile of an insulin pump according to one or more embodiments shown and described herein.

FIG. 3 depicts a method 90 for adjusting an insulin delivery profile of an insulin pump. The insulin pump may be configured to automatically deliver insulin to a person having diabetes based on an operating time of the internal clock and a delivery time of an insulin delivery profile. At act 92, the method 90 receives a local time zone time from an external local clock. As previously discussed herein, the external local clock may be derived from a global positioning system, a wireless computer network, a cellular network, a blood glucose meter, a smart phone, or the person. In addition, the external local clock may be derived from a wired computer network, such as an Ethernet network. Other types of wired computer networks may be used as well. At act 94, the method 90 determines whether the operating time of the internal clock differs from the local time zone time by at least a first predetermined amount of time.

Still referring to FIG. 3, at act 96, the method 90 requests the person provide a time adjustment value when the operating time of the internal clock differs from the local time zone by at least the first predetermined amount of time. At act 98, the method 90 receives the time adjustment value from the person. Finally, at act 100, the method 90 adjusts the one or more delivery times of the insulin delivery profile based on the time adjustment value when received. The acts of the method 90 may be performed in any suitable order.

Act 92 may comprise periodically requesting the local time zone time from the external local clock. For example, the method 90 may request the local time zone time every one minute. Act 96 may comprise displaying a message on a blood glucose meter which is in electrical communication with the insulin pump. The message may request that the person provide a time adjustment value. Act 98 may comprise inputting the time adjustment value (by the person) into the blood glucose meter and transmitting the time adjustment value to the insulin pump. The transmission may be wireless, such as Bluetooth® or other suitable technology. Act 100 may comprise limiting the time adjustment value to the difference between the operating time of the internal clock and the local time zone time of the external clock.

The first predetermined time of the method 90 may be 15 minutes or some other suitable value. The method 90 may further comprise delaying at least a second predetermined amount of time before requesting the person provide a time adjustment value. The second predetermined amount of time may be 24 hours or any suitable value. The method 90 may additionally comprise recording a time-stamp of both the local time zone time and the operating time when the insulin is delivered to the person. This may permit (when the operating time and the local time zone time are different) the insulin pump to remove any ambiguity as to when the insulin was delivered to the person. For example, if the person travels from the United States to Western Europe, the operating time may be 7:05 pm, while the local time zone time may be 1:05 pm (the same day) when a delivery of insulin is made. Recording a time-stamp of both time may permit the person or a health care provider to later examine the records and, without ambiguity, determine that insulin was delivered to the person at 7:05 pm insulin pump time, which is the same time as 1:05 pm Middle European Time.

The internal clock of the insulin pump may maintain the local time, day, and year, wherein "local" means the time zone in which the insulin pump is located. The internal clock may alternatively maintain the UTC time, day, and year. In this case, the insulin pump may contain one or more registers indicating the time difference between the local time and the UTC time. For example, the Eastern Time Zone of the United States is five hours earlier than UTC during standard time and four hours during daylight savings time (which occurs during the summer). If the internal clock maintains UTC time, the insulin pump may display only the operating time to the person.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It should now be understood that the systems and methods described herein may recognize when the person's local time has changed and permit the person to adjust the internal clock of the insulin pump, based on the person's preference and the difference in time between the internal clock of the insulin pump and the local time zone.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. An insulin pump for automatically delivering insulin to a person having diabetes and configured to receive at least a local time zone time from an external local clock, the insulin pump comprising:
   an internal clock providing an operating time;
   a delivery module for delivering the insulin to the person;
   memory storing an insulin delivery profile comprising one or more delivery times;
   a wireless communication module configured to wirelessly receive the local time zone time from the external local clock; and
   a processor in electrical communication with the internal clock, the memory for reading the insulin delivery profile, the delivery module, and the wireless communication module, wherein the processor:
   automatically causes the delivery module to deliver the insulin to the person when a delivery time of the insulin delivery profile that is read from memory by the processor matches the operating time of the internal clock,
   receives the local time zone time from the wireless communication module,
   makes a request for the person to provide a time adjustment value when the operating time of the internal clock differs from the local time zone time by at least a first predetermined amount of time,
   receives the time adjustment value from input provided by the person, and
   adjusts the one or more delivery times of the insulin delivery profile based on the time adjustment value when received.

2. The insulin pump of claim 1, wherein the external local clock is derived from a global positioning system, a wireless computer network, a cellular network, a blood glucose meter, or a smart phone.

3. The insulin pump of claim 1, wherein the processor periodically requests a local time zone time update from the wireless communication module.

4. The insulin pump of claim 1, wherein the processor is configured to limit the time adjustment value to the difference between the operating time of the internal clock and the local time zone time of the external local clock.

5. The insulin pump of claim 1, wherein the first predetermined amount of time is 15 minutes.

6. The insulin pump of claim 1, wherein the first predetermined amount of time is settable by the person.

7. The insulin pump of claim 1 further comprising a travel mode of operation, wherein the first predetermined amount of time is set to a travel value, and a home mode of operation, wherein the first predetermined amount of time is set to a home value.

8. The insulin pump of claim 1, wherein the processor delays making a request for the person to provide a time adjustment value until after the difference has persisted for at least a second predetermined amount of time.

9. The insulin pump of claim 8, wherein the second predetermined amount of time is 24 hours.

10. The insulin pump of claim 1, wherein the processor is configured to record a time-stamp of both the local time zone time and the operating time upon causing the delivery module to deliver the insulin to the person.

11. The insulin pump of claim 1, wherein at least one of the one or more delivery times of the insulin delivery profile is a basal rate delivery time, and the basal rate delivery time is adjusted when the insulin delivery profile is adjusted.

12. A system for automatically delivering insulin to a person having diabetes and configured to receive at least a local time zone time from an external local clock, the system comprising:
   an insulin pump having:
      an internal clock providing an operating time,
      a delivery module for delivering the insulin to the person according to an insulin delivery profile comprising one or more delivery times,
      memory storing the insulin delivery profile, and
      a first processor in electrical communication with the internal clock, the memory for reading the insulin delivery profile, and the delivery module; and
   a blood glucose (bG) meter in communication with the insulin pump via a wireless communication link, the bG meter having an input device, a display, a wireless communication module, and a second processor in electrical communication with the input device, the display, the wireless communication module, wherein:
the second processor:
receives the operating time of the internal clock of the insulin pump via the wireless communication link,
receives the local time zone time from the external local clock via the wireless communication module or from the person via the input device,
determines whether times of the local time zone time and the operating time differ by at least a first predetermined amount of time,
displays a request on the display for a time adjustment value from the person representing an amount of time to adjust the one or more delivery times of the insulin delivery profile when the operating time of the internal clock differs from the local time zone time by at least the first predetermined amount of time,
receives the time adjustment value via the input device,
sends the time adjustment value when received to the insulin pump via the wireless communication link, and
the first processor adjusts the one or more delivery times of the insulin delivery profile based on the time adjustment value sent from the bG meter.

13. The system of claim 12, wherein the external local clock is derived from a global positioning system, a wireless computer network, a cellular network, another blood glucose meter, or a smart phone.

14. The system of claim 12, wherein the second processor periodically requests a local time zone time update from the wireless communication module.

15. The system of claim 12, wherein the first or the second processor is configured to limit the time adjustment value to the difference between the operating time of the internal clock and the local time zone time of the external local clock.

16. The system of claim 12, wherein the first predetermined amount of time is 15 minutes.

17. The system of claim 12, wherein the first predetermined amount of time is settable by the person.

18. The system of claim 12, wherein the insulin pump further comprises a travel mode of operation, wherein the first predetermined amount of time is set to a travel value, and a home mode of operation, wherein the first predetermined amount of time is set to a home value.

19. The system of claim 12, wherein the second processor delays making a request for the person to provide a time adjustment value until after the difference has persisted for at least a second predetermined amount of time.

20. The system of claim 19, wherein the second predetermined amount of time is 24 hours.

21. The system of claim 12, wherein the first or the second processor is configured to record a time-stamp of both the local time zone time and the operating time when the insulin is delivered to the person.

22. The system of claim 12, wherein the wireless communication link is Bluetooth.

23. The system of claim 12, wherein at least one of the one or more delivery times of the insulin delivery profile is a basal rate delivery time, and the basal rate delivery time is adjusted when the insulin delivery profile is adjusted.

24. A method for adjusting an insulin delivery profile of an insulin pump, wherein the insulin pump is configured to automatically deliver insulin to a person having diabetes based on an operating time of an internal clock and the insulin delivery profile comprising one or more delivery times, and the method comprises:
receiving a local time zone time from an external local clock;
determining whether the operating time of the internal clock differs from the local time zone time by at least a first predetermined amount of time;
requesting the person provide a time adjustment value when the operating time of the internal clock differs from the local time zone time by at least the first predetermined amount of time;
receiving the time adjustment value from the person; and
adjusting the one or more delivery times of the insulin delivery profile based on the time adjustment value when received.

25. The method of claim 24, wherein the external local clock is derived from a global positioning system, a wireless computer network, a wired computer network, a cellular network, a blood glucose meter, a smart phone, or the person.

26. The method of claim 24, wherein receiving the local time zone time from the external local clock comprises periodically requesting the local time zone time.

27. The method of claim 24, wherein adjusting the operating time of the internal clock comprises limiting the time adjustment value to the difference between the operating time of the internal clock and the local time zone time of the external local clock.

28. The method of claim 24, wherein the first predetermined amount of time is 15 minutes.

29. The method of claim 24 further comprising receiving the first predetermined amount of time from the person.

30. The method of claim 24 further comprising selecting a travel mode of operation, wherein the first predetermined amount of time is set to a travel value, and a home mode of operation, wherein the first predetermined amount of time is set to a home value.

31. The method of claim 24 further comprising delaying at least a second predetermined amount of time before requesting the person provide a time adjustment value.

32. The method of claim 31, wherein the second predetermined amount of time is 24 hours.

33. The method of claim 31 further comprising receiving the second predetermined amount of time from the person.

34. The method of claim 24 further comprising recording a time-stamp of both the local time zone time and the operating time when the insulin is delivered to the person.

35. The method of claim 24 wherein requesting the person provide a time adjustment value comprises displaying a message on a blood glucose meter in electrical communication with the insulin pump.

36. The method of claim 35, wherein receiving the time adjustment value comprises inputting the time adjustment value into the blood glucose meter and transmitting the time adjustment value to the insulin pump.

37. The method of claim 24, wherein at least one of the one or more delivery times of the insulin delivery profile is a basal rate delivery time, and the basal rate delivery time is adjusted when the insulin delivery profile is adjusted.

* * * * *

UNITED STATES PATENT AND TRADEMARK OFFICE
CERTIFICATE OF CORRECTION

| | | |
|---|---|---|
| PATENT NO. | : 8,092,428 B2 | Page 1 of 1 |
| APPLICATION NO. | : 12/645587 | |
| DATED | : January 10, 2012 | |
| INVENTOR(S) | : Blaine Edward Ramey et al. | |

It is certified that error appears in the above-identified patent and that said Letters Patent is hereby corrected as shown below:

On the title page, item [75]: Inventor, "James Pauley" should read --James L. Pauley, Jr.--

Col. 4, Line 24, "both in known the" should read --both known in the--

Col. 5, Line 29, "year.)" should read --year).--

Col. 6, Line 47, "of a day.)" should read --of a day).--

Col. 7, Line 14, ", the if the" should read --, if the--

Col. 8, Line 63, "and or" should read --and/or--

Col. 9, Line 53, "of a day.)" should read --of a day).--

Signed and Sealed this
Twenty-eighth Day of August, 2012

David J. Kappos
*Director of the United States Patent and Trademark Office*